US00PP35192P2

(12) United States Plant Patent
Hansen

(10) Patent No.: US PP35,192 P2
(45) Date of Patent: May 23, 2023

(54) ***MONARDA* PLANT NAMED 'LAVENDER TAFFETA'**

(50) Latin Name: ***Monarda* hybrid**
Varietal Denomination: Lavender Taffeta

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,782

(22) Filed: Nov. 22, 2022

(51) Int. Cl.
*A01H 5/02* (2018.01)
*A01H 6/50* (2018.01)

(52) U.S. Cl.
USPC ..... Plt./455

(58) Field of Classification Search
USPC ..... Plt./455
See application file for complete search history.

*Primary Examiner* — Susan McCormick Ewoldt

(57) ABSTRACT

The new and distinct cultivar of ornamental cultivar of Bee Balm *Monarda* plant named 'Lavender Taffeta' has medium-height, winter hardy, dense, vigorous clumping habit, dark green glossy foliage that exhibits strong resistance to powdery mildew, and numerous large flower heads of dark lavender-purple-colored flowers creating excellent flower coverage. The lower petals have darker strong purplish-red spots, and each flower head is subtended by burgundy-colored bracts. The new plant is attractive and useful in the garden landscape as a specimen, en masse, or as a container plant.

1 Drawing Sheet

Botanical classification: *Monarda* hybrid.
Variety denomination: 'Lavender Taffeta'.

STATEMENT REGARDING PRIOR DISCLOSURES UNDER 37 CFR 1.77(B)(6)

The first non-enabling information of the new plant was made on Dec. 1, 2021, in the form of photographs and a brief description on websites operated by Walters Gardens, Inc. and Proven Winners®, followed on Jun. 8, 2022, as a photograph and brief description in the "Walters Gardens 2022-2023 Catalog." Walters Gardens, Inc and Proven Winners® obtained the plant and all information relating thereto, from the inventor. The first sales of the new plant were on Jul. 11, 2022, by Walters Gardens, Inc. which obtained the plants and all information about the plants from the inventor. No plants of *Monarda* 'Lavender Taffeta' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102b exception.

BACKGROUND OF THE INVENTION

The present invention relates to the new and distinct cultivar of bee balm plant, botanically known as *Monarda* 'Lavender Taffeta', and hereinafter also referred to solely as the cultivar 'Lavender Taffeta' or the "new plant". The new plant was selected from cross on Jun. 22, 2015, between 'Bubblegum Blast' U.S. Plant Pat. No. 27,497 as the female parent and 'Leading Lady Plum' U.S. Plant Pat. No. 26,447 as the male parent at a hybridizing plot of a wholesale perennial nursery in Zeeland, Mich., USA. The new plant was a single seedling selection originally made in the summer of 2017 from the seeds that were sown in the fall of 2015 and the plant was assigned the breeder code of 15-6-5 through the subsequent trialing process. Further selection was completed in the research facility of a wholesale perennial nursery in Zeeland, Mich. in the summer of 2019.

The new plant has been asexually propagated first by division in the summer of 2017 followed by shoot tip cuttings originally in 2019 at the same nursery in the greenhouses in Zeeland, Mich., and the subsequent asexually propagated plants have been found to be stable, true to type, and identical to the original selection.

BRIEF SUMMARY OF THE PLANT

*Monarda* 'Lavender Taffeta' is unique from its parents and all other Bee Balm plants known to the inventors. The nearest comparison varieties are: 'Electric Neon Purple' U.S. Plant Pat. No. 34,512, 'Leading Lady Amethyst' U.S. Plant Pat. No. 34,371, 'Pardon My Lavender' U.S. Plant Pat. No. 28,770, and 'Pardon My Lavender II' U.S. Plant Pat. No. 34,131.

'Electric Neon Purple' has bright fuchsia-purple flowers without spotting on the lower petal. 'Leading Lady Lavender' has a shorter habit with flowers that are a light amethyst-purple. 'Pardon My Lavender' has a smaller habit, lighter lavender-pink flowers without the darker spots on the lower petal, and without the anthocyanin on the bracts and foliage. 'Pardon My Lavender II' has a shorter habit, lavender-purple flowers and lacks the darker spots on the lower petal. The male parent, 'Leading Lady Plum' U.S. Plant Pat. No. 26,447, has a more compact shorter habit with flowers that are magenta-purple.

The female parent, 'Bubblegum Blast' U.S. Plant Pat. No. 27,497 has a slightly smaller habit and hot pink flowers without the darker spots on the lower petals. The male parent plant has a shorter habit and the flower color is more purplish color and less reddish.

The following are traits of *Monarda* 'Lavender Taffeta' that in combination distinguish it from all other bee balm known to the inventor:

1. Medium-height, winter-hardy, dense, vigorous, clumping habit;
2. Dark-green glossy leaves that are strongly resistant to powdery mildew;
3. Large flower heads of dark, lavender-purple-colored flowers for a long period in summer with excellent flower coverage;
4. Lower flower petal has darker spots of strong purplish-red;
5. Flower heads are subtended by burgundy-colored bracts.

BRIEF DESCRIPTION OF THE DRAWINGS

The photographs of the new plant demonstrate the unique traits of 'Lavender Taffeta' and the overall appearance of two-year-old plants in the full-sun, outdoor, research facility of a wholesale perennial nursery in Zeeland, Mich. The colors are as accurate as reasonably possible with color reproductions. Variations in the ambient light spectrum, source, intensity, and direction may cause the appearance of minor variations in color.

DETAILED BOTANICAL DESCRIPTION

Figure 1:
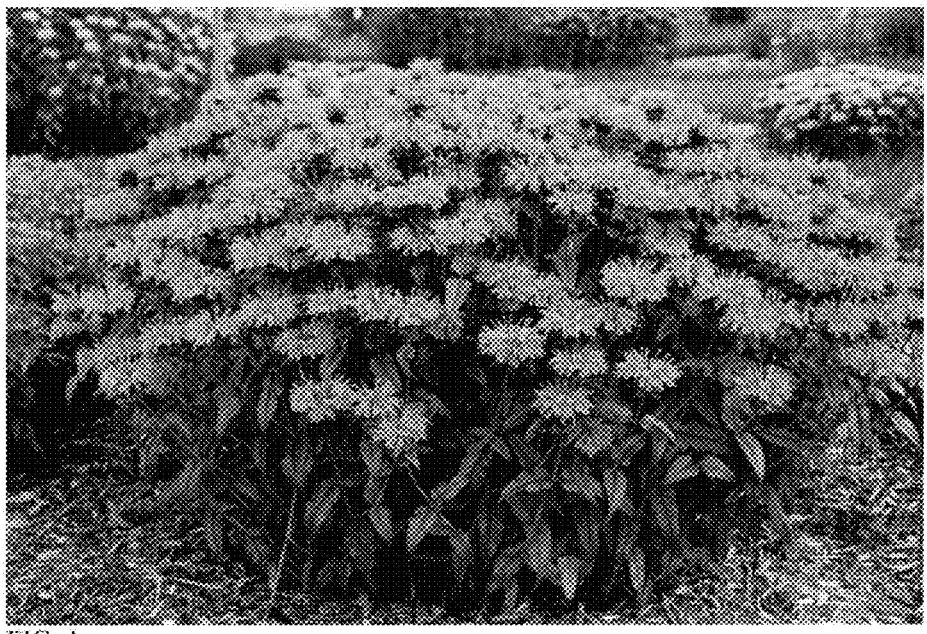
FIG. 1 shows the new plant in flower in the research facility.
Figure 2:
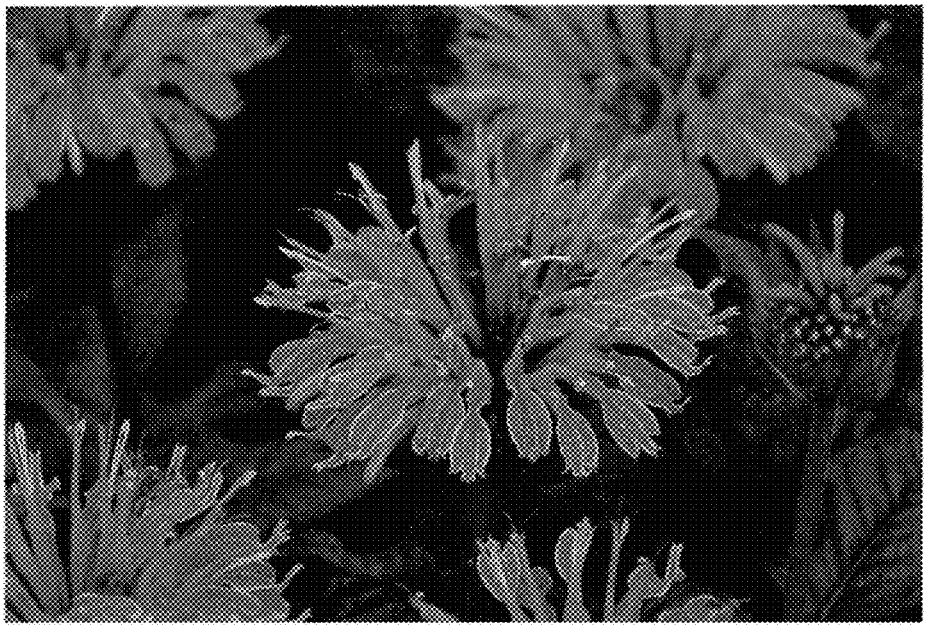
FIG. 2 shows a close-up of the flowers.

The following descriptions and color references are based on the 2015 edition of The Royal Horticultural Society Colour Chart except where common dictionary terms are used. *Monarda* 'Lavender Taffeta' has not been observed under all possible environments. The phenotype may vary slightly with different growing environments such as temperature, light, fertility, soil pH, moisture, and maturity levels, but without any change in the genotype. The following observations and size descriptions are based on two-year-old plants in a display garden and one-year-old plants grown in a partially shaded greenhouse at a nursery in Zeeland, Mich. with supplemental fertilizer and water as needed.

Botanical classification: *Monarda* hybrid including the species *didyma, bradburiana*, and *fistulosa;*

Parentage: The female parent is 'Bubblegum Blast' and the male parent is 'Leading Lady Plum';

Plant habit: Winter-hardy herbaceous perennial, compact, producing several stems spreading by short rhizomes; to 66 cm tall at flowering and 76 cm wide; flowering beginning early-summer in Michigan and continuing for about 4 weeks;

Propagation: Stem cuttings;

Time to produce finished crop in 3.8-liter pots: About 8 to 10 weeks; vigorous rate of growth;

Root: Fine, fibrous, and freely branching; color creamy white to tan depending on soil type;

Leaves: Simple; lanceolate; opposite; serrated; finely and puberulent adaxial and abaxial; lustrous adaxial, matte below; acute apex, rounded to cordate base; to about 100 mm long and about 53 mm wide, decreasing distally, average about 88 mm long and 46 mm wide;

Leaf color: Young expanding leaves between RHS 146A and RHS 137A on adaxial surface, abaxial surface nearest RHS 146A; mature adaxial leaves between RHS 139A and RHS NN137A and abaxial leaves between RHS 137B and RHS NN137C;

Foliage fragrance: Pleasant lemony;

Veins: Pinnate; adaxial glabrous and minutely puberulent abaxial; slightly sunken above and costate below;

Vein color: Mature adaxial proximal midrib nearest RHS 195B, distal midrib and primary veins nearest RHS N148D; mature abaxial proximal midrib between RHS 145C and RHS 145D, primary veins near midrib between RHS 145D and RHS 146D transitioning to nearest RHS 146B distally; emerging adaxial midrib and primary veins nearest RHS 146D with the proximal midrib heavily blushed with nearest RHS 187B, emerging abaxial proximal midrib between RHS 146D and RHS 145C, distal midrib and veins nearest RHS 146B;

Petiole: Puberulent; slightly concavo-convex; to about 16 mm long and 3 mm across, decreasing distally;

Petiole color: Adaxial nearest RHS 196B with faint anthocyanin of nearest 187B, abaxial center nearest RHS 145C, and margin nearest RHS 137A;

Stems: Quadrangular; puberulent; to about 63 cm long and 4 mm across at base;

Stem color: Basal portion nearest RHS 146D, distal portion nearest RHS 146B with heavy anthocyanin blush to nearly solid nearest RHS 187B with high sun exposure;

Branches: In middle and distal nodes; quadrangular; puberulent; typically, three to six per main stem at initial flowering; about 2 mm across at base and to about 22 cm long;

Branch color: Basal portion nearest RHS 146D, distal portion nearest RHS 146B with heavy anthocyanin blush to nearly solid nearest RHS 187B with high sun exposure;

Nodes: About 8 to 10 per stem;

Node color: Nearest RHS 146C with thin bands of nearest RHS 187B above and below when exposed to high sun exposure;

Flowers: Single; labiate; actinomorphic; flowers arranged in terminal verticillate head about 80 mm across and 35 mm tall, opening from the center and progressing outwardly and downwardly; individual flowers to about 41 mm long to exserted pistil; corolla to about 37 mm long, 18 mm tall and 7 mm across; numerous, about 120 to 250 flowers per head; slightly arcuate distally; self-cleaning;

Flower lasting: Individual flowers persisting about 5 days in Michigan, head remains effective for 2 to 3 weeks;

Flower period: Usually late June to late July; about four weeks;

Flower fragrance: None observed;

Flower attitude: Initial flowers upwardly to outwardly, outer flowers outwardly to slightly drooping;

Buds one to two days prior to opening: Narrowly clavate; tubular; rounded apex; arcuate slightly downward in distal half; about 31 mm long, about 3 mm across in the middle and about 4 mm tall;

Bud color one to two days prior to opening: Dorsal portion nearest RHS NN78C and ventral portion nearest RHS N74D with spots of nearest RHS N79D;

Petals: Bilabiate; fused in proximal 21 mm, split in two in about the distal 16 mm; glabrous adaxial except pubescent in center 3 to 5 mm of lower lip, puberulent abaxial;

Dorsal labium: Straight with slight reflex in distal 2 mm; folded into a hood about 16 mm long from fusion and 3 mm across and 2 mm tall just distal fusion;

Ventral labium: About 18 mm long from fusion; comprising three apical lobes including two side lobes about 1 mm long and 2 mm across having rounded apex entire margin, and center lobe to about 5 mm long and 2 mm wide, folded upward about 90°, with emarginate apex split in distal 0.5 mm, and entire margin; with dark spots of typically 0.5 to 1 mm diameter across;

Corolla tube color: Basal adaxial and abaxial 6 mm of nearest RHS N155C, abaxial distal and dorsal portion of nearest RHS 72B, abaxial distal ventral portion nearest RHS N74C; unchanged with age;

Dorsal labium color: Adaxial distal portion nearest RHS 72B in young flower and nearest RHS 77B in older flower; abaxial distal portion nearest RHS N78A in young flower and nearest RHS 72B in older flower;

Ventral labium color: Adaxial young flower between RHS N78B and RHS N78C with spots of nearest RHS 72A and adaxial mature flower nearest RHS N78B with spots of nearest RHS 72A; abaxial distal free portion of young flower nearest RHS N74C with spots of nearest RHS 72B, and mature flower nearest RHS N74B with spots showing through from adaxial side of nearest RHS 70A; adaxial and abaxial side lobes nearest RHS 74C without spots; central lobe adaxial nearest RHS N74C with middle having nearly overlapping spots of nearest RHS 72A, and apex nearest RHS N74D, abaxial central lobe nearest RHS N74D;

Floral bracts: Two sets, between 6 and 10 in each set subtending flower head; proximal set ovate with narrowly acute apex, sessile rounded base, and finely serrulate and micro-ciliolate margin, sides reflexed; to about 50 mm long and 29 mm wide; distal set lanceolate to linear with narrowly acute apex, sessile acuminate base, and ciliolate margin; to about 19 mm long and 3 mm wide near base;

Floral bract color: Proximal set adaxial variable, nearest RHS 139A to solid nearest RHS N186C, abaxial nearest RHS 137A to nearest RHS 137B with moderate blush of nearest RHS N186C; distal set adaxial and abaxial portion nearest RHS 146D with adaxial distal two-thirds between RHS 187B and RHS 187C and distal two-thirds abaxial nearest RHS N186C;

Androecium: Two;

*Filaments*.—Two, to about 35 mm long by 0.3 mm diameter; adnate to inner corolla tube in proximal 15 mm; color proximally nearest RHS 76D, distally between RHS 72C and RHS 72D.

*Anther*.—Two; connate; oblong-elliptic, dorsifixed, longitudinal; 3 mm by 1 mm; color nearest RHS N77B.

*Pollen*.—Abundant, elliptic to globose, less than 0.1 mm; color between RHS 13B and RHS 13C.

Gynoecium: One per flower; about 41 mm long at maturity, exserted;

*Style*.—About 39 mm by 0.3 mm; color base nearest RHS NN155D, distal two-thirds nearest RHS N75D.

*Stigma*.—Split in two in the distal 1 mm, 0.2 mm in diameter; color between RHS 77A and RHS 77B.

*Ovary*.—1.0 mm by 0.75 mm; color between RHS 143D and RHS 144B.

*Calyx*.—Tubular; consisting of five fused sepals; about 11 mm long and 4 mm diameter at apex with calyx tube base about 1.5 mm diameter.

Sepals: Five; apiculate apex; margin micro-serrulate; basal 9 mm fused forming corolla tube; about 11 mm long and 0.5 mm across at fusion; glabrous adaxial and abaxial;

Sepal color: Adaxial and abaxial distal free portion nearest RHS N186B; adaxial proximally nearest RHS 194D, distally nearest RHS 148C with darker veins nearest RHS 147A, abaxial basal portion between RHS 145D and RHS 146D, transitioning in the central portion to nearest RHS 147B, and distal portion nearest RHS 187B with darker veins distally of nearest RHS 187A;

Pedicel: Short, cylindrical; glabrous; about 1 mm long and 0.5 mm diameter;

Pedicel color: Nearest RHS 147C;

Peduncle: Pubescent; stiff; strong; erect; hollow; quadrangular to about 2.5 mm across and about 70 mm long just above last leaves;

Peduncle color: Nearest RHS 146C;

Fruit: Single nutlet, elliptical, about 1.0 mm long and 0.7 mm wide; color nearest RHS 202A; Hardiness: the new plant grows best with plenty of moisture and adequate drainage; hardy to at least from USDA zone 4 through 8;

Disease and pest resistance: Demonstrated moderate powdery mildew resistance (*Sphaerotheca pannosa* var. *rosa*).

I claim:

1. A new and distinct cultivar of ornamental Bee Balm *Monarda* plant named 'Lavender Taffeta', as herein described and illustrated.

* * * * *